(12) United States Patent
Garcia Rojas et al.

(10) Patent No.: US 10,701,876 B2
(45) Date of Patent: Jul. 7, 2020

(54) PRODUCTION OF PLANTS USING SOMATIC EMBRYOGENESIS

(71) Applicant: MARS, INCORPORATED, McLean, VA (US)

(72) Inventors: Claudia Yanet Garcia Rojas, McLean, VA (US); Cristiano Villela Dias, McLean, VA (US); Jean-Philippe Marelli, McLean, VA (US)

(73) Assignee: Mars, Incorporated, McLean, VI (US)

( * ) Notice: Subject to any disclaimer, the term of this patent is extended or adjusted under 35 U.S.C. 154(b) by 0 days.

(21) Appl. No.: 15/037,972

(22) PCT Filed: Nov. 19, 2014

(86) PCT No.: PCT/US2014/066453
§ 371 (c)(1),
(2) Date: May 19, 2016

(87) PCT Pub. No.: WO2015/077365
PCT Pub. Date: May 28, 2015

(65) Prior Publication Data
US 2016/0286749 A1   Oct. 6, 2016

(30) Foreign Application Priority Data
Nov. 19, 2013  (GB) .................................. 1320387.2

(51) Int. Cl.
*A01H 4/00* (2006.01)
*A23G 1/30* (2006.01)
(52) U.S. Cl.
CPC .............. *A01H 4/005* (2013.01); *A23G 1/30* (2013.01)
(58) Field of Classification Search
None
See application file for complete search history.

(56) References Cited

U.S. PATENT DOCUMENTS

| | | | | |
|---|---|---|---|---|
| 5,312,801 | A * | 5/1994 | Sondahl | A01H 4/00 435/430.1 |
| 6,150,587 | A * | 11/2000 | Guiltinan | A01H 4/001 435/419 |
| 8,921,087 | B2 | 12/2014 | Florin et al. | |
| 2010/0236143 | A1* | 9/2010 | Florin | A01H 4/005 47/58.1 SE |

FOREIGN PATENT DOCUMENTS

| | | |
|---|---|---|
| EP | 2067401 A1 | 6/2009 |
| WO | WO 1993/12645 A1 | 7/1993 |
| WO | WO 2012/146921 A1 | 11/2012 |

OTHER PUBLICATIONS

Garcés et al., 2010, Special Abstracts / Journal of Biotechnology 150S (2010) S1-S576: P-P&F.8.*
Kintzios et al., 1998, Acta Hort. 461: 427-432.*
Processing Cocoa, International Cocoa Organization , Jun. 7, 2013.*
Maximova et al., 2002, Efficiency, genotypic variability, and cellular origin of primary and secondary somatic embryogenesis of Theobroma cacao L., In Vitro Cell Dev. Biol. 38: 252-259.*
Australian Examination Report issued in Australian Patent Application No. 2014353082 dated Dec. 21, 2016.
Extended European Search Report issued in European Patent Application No. 14863967.7 dated Mar. 31, 2017.
Lopez-Baez et al, "Somatic embryogenesis and plant regeneration from flower parts of cocoa Theobroma cacao L.," Comptes rendus des seances de l'academie des sciences. serie III: Sciences de la VIE, Jan. 1, 1993, pp. 579-584, vol. 316, Elsevier Amsterdam, NL.
Quirós, "Evaluación de dos protocolos para la inducción de embriogénesis somática en clones de cacao (Theobroma cacao L.) seleccionados por el Programa de Mejoramiento Genético de Cacao del CATIE," Jan. 1, 2013, 96 pages.
Haensch, "Influence of 2,4-D and BAP on callus growth and the subsequent regeneration of somatic embryos in long-term cultures of Pelagonium x domesticum cv. Madame Loyal," Electronic Journal of Biotechnology, Jan. 15, 2007, pp. 69-77, vol. 10, No. 1.
International Search Report and Written Opinion issued in PCT/US2014/066453 dated Feb. 19, 2015.
Li et al., "Somatic embryogenesis and plant regeneration from floral explants of cacao (Theobroma cacao I.) using thidiazuron," In Vitro Cell Dev. Biol. Plant, Oct.-Dec. 1998, pp. 293-299, vol. 3, No. 4.
Maximova et al, "Efficiency, genotypic variability, and cellular origin of primary and secondary somatic embryogenesis of Theobroma cacao I.," In Vitro Cell Dev. Biol. Plant, May-Jun. 2002, pp. 252-259, vol. 38.
Niemenak et al, "Regeneration of somatic embryos in Theobroma cacao L. in temporary immersion bioreactor and analyses of free amino acids in different tissues," Plant Cell Reports, Jan. 10, 2008, pp. 667-676, vol. 27.
International Preliminary Report on Patentability received for PCT Patent Application No. PCT/US2014/066453, dated May 24, 2016, 6 pages.
International Search Report for PCT Patent Application No. PCT/US2014/066453, dated Jan. 29, 2015, 3 pages.
Written Opinion for PCT Patent Application No. PCT/US2014/066453, dated Jan. 29, 2015, 5 pages.

(Continued)

Primary Examiner — Bratislvav Stankovic
(74) Attorney, Agent, or Firm — Morrison & Foerster LLP

(57) ABSTRACT

A process for propagating Theobroma cacao L. is described. The process uses direct or indirect somatic embryogenesis to produce primary embryos from explant material, and then applies direct somatic embryogenesis to the resulting primary embryos to produce secondary embryos. These may be matured, pre-germinated, and germinated to form plantlets. Plants, plants bearing fruit, and plant materials are also provided, as well as methods for processing the fruit of the plants to generate cocoa products.

37 Claims, 6 Drawing Sheets

(56) References Cited

OTHER PUBLICATIONS

Office Action received for European Patent Application No. 14863967.7, dated May 8, 2018, 7 pages.
Traore et al., "Effects of Carbon Source and Explant Type on Somatic Embryogenesis of Four Cacao Genotypes", HortScience, vol. 41, No. 3, Jun. 2006, pp. 753-758.

* cited by examiner

PRODUCTION OF PLANTS USING SOMATIC EMBRYOGENESIS

CROSS-REFERENCE TO RELATED APPLICATIONS

This application is a National Stage entry of International Application No. PCT/US2014/066453, filed on Nov. 19, 2014, which claims the benefit of priority from British Patent Application No. 1320387.2, filed on Nov. 19, 2013. The entirety of the priority application is incorporated herein by reference.

FIELD OF THE INVENTION

The present invention relates generally to methods of propagating *Theobroma cacao* plants in vitro. The methods include in vitro multiplication of direct somatic embryos (DSE) or indirect somatic embryos (ISE) using direct somatic embryogenesis, and plant regeneration, as well as plants, plants bearing fruit, and plant materials obtained thereby. Methods for processing the fruit of the plants to generate cocoa products, particularly edible cocoa products are also provided.

BACKGROUND OF THE INVENTION

*Theobroma cacao* L. is a tropical tree originating in the Amazon, where it occurred naturally in the shade of the tropical rainforests. Cacao sub-products like butter and powder are produced as principal components of chocolate, and contain with important compounds for nutrition as polyphenols and flavonoids, among others. However, bean production is decreasing due to the fact that many plantations are old and unproductive. Propagation of cacao has been traditionally carried out through classical propagation methods, such as grafting or rooted-cuttings, but those are not sufficient for obtaining large amounts of planting material with the desired genetic quality and plant health.

In the search for solutions to this problem, somatic embryogenesis is one of the vegetative methods for propagation of cacao that shows potential for providing large quantities of high-quality planting material. Somatic embryos are formed from plant cells that are not normally involved in the development of embryos, i.e., ordinary plant tissue. Applications of the somatic embryogenesis process include: clonal propagation of genetically uniform plant material; elimination of viruses; provision of source tissue for genetic transformation; generation of whole plants from single cells; and development of synthetic seed technology.

Somatic embryogenesis is a type of clonal propagation where competent cells in the somatic tissue can develop into embryos and subsequently convert into plants. In indirect somatic embryogenesis, cells derived from competent source tissue can be cultured to form an undifferentiated mass of cells called a callus. Plant growth regulators in the tissue culture medium can be manipulated to induce callus formation and subsequently changed to induce embryos to form from the callus. The ratio of different plant growth regulators required to induce callus or embryo formation varies with the type of plant.

This method offers significant technological advantages, because it is possible to obtain a large amount of disease-free planting material with good agronomic characteristics and genetic stability. However, tissue culture techniques can be cumbersome and there is significant variation between the protocols and conditions that are required to produce different plant types or species.

The majority of the work to date in micropropagation of cacao through somatic embryogenesis uses the technique of indirect embryogenesis (Maximova et al., 2002 *In Vitro Cell Dev. Biol Plant* 38:252-259 and WO 2009/071254) in which undifferentiated calluses are obtained as a source of primary embryos.

WO 2009/071254 describes *Theobroma cacao* L. propagation by indirect somatic embryogenesis in solid or liquid media cocoa flower buds and leaves which are subjected to:
  i) primary embryogenesis in the dark in a solid culture medium for 5 to 15 weeks for causing induction and expression to produce primary embryos,
  ii) secondary embryogenesis
    (a) in which the primary embryos are treated in the dark in solid or liquid media culture medium for 10 to 25 weeks to produce and multiply embryogenesis callus followed by
    (b) treatment of the embryogenesis callus in the dark in a suitable liquid culture medium for 1 to 6 weeks for causing expression of the embryogenesis callus to produce further new secondary embryos,
  iii) pre-germination of the secondary embryos in a Petri dish on a solid medium, or in a bioreactor in a liquid medium for 3 to 12 weeks, into pre-germinated secondary embryos at the cotyledonary stage,
  iv) ex vitro germination of the pre-germinated secondary embryos at the cotyledonary stage by sowing directly on a culture substrate in the greenhouse to produce the plantlets, and
  v) development of the plantlets.

However, such systems require a long period to obtain somatic embryos and regenerated plants, and can result in a high amount of abnormal embryos. Furthermore, because of the reliance on formation of callus tissue, there is a higher probability of somaclonal variation among the regenerated plants.

In the approach of direct embryogenesis, somatic embryos may be derived from plant tissues comprising differentiated cells. The differentiated cells may include specialized cells such as the differentiated cells of cicatricial callus that forms on the epidermis of a plant, for example, in response to a wound. The differentiated cells of the explant material used in direct somatic embryogenesis is therefore different from the undifferentiated callus used in indirect somatic embryogenesis. The method comprises the cultivation of explants in culture media supplemented only with cytokinin, or the combination of auxin and cytokinin (Dublin, *Café Cacao Thé*, Paris, 25(4), 237-241, 1981; Pierson et al., *Protoplasma* 115, 208-216, 1983). Some authors, such as Dublin (1981), suggest that propagation by direct somatic embryogenesis is suitable for keeping the stability of the donator genotype in some species, such as coffee.

Typically processes based upon direct somatic embryogenesis involve the following sequence of steps:
  i) Induction of direct somatic embryogenesis
  ii) Development of somatic embryos
  iii) Multiplication of direct somatic embryos
  iv) Germination of somatic embryos
  v) Conversion in plants of somatic embryos.

However, previous attempts to apply this technique to the propagation of cacao have not been satisfactory. For example, it was reported by Litz, R. E. ("Tissue Culture Studies with *T. cacao*," *Cacao Biotechnology Symposium*, Pennsylvania State University, U.S.A. 1986) that a low frequency of somatic embryogenesis from young leaves was obtained using a semi-solid MS medium (Murashige and Skoog, 1962), supplemented with sucrose, and high levels of the synthetic auxin 2,4-dichlorophenoxyacetic acid (2,4-D) and the synthetic cytokinin 6-benzylaminopurine (BAP). The somatic embryos developed only to the heart stage. Some direct embryogenesis was observed at the base of young petal explants from immature flowers of cacao after three weeks of culture (Sondahl, M. R. et al. "Somatic Embryogenesis and Plan Regeneration of cacao." *Acta Hort.* Republic of South África. 1993), when grown in liquid medium with different combinations of BAP, indole-3-acetic acid (IAA), gibberellic acid (GA3), abscisic acid (ABA), and 2,4-D, supplemented with coconut water and kept in the dark. The response was dependent on genotype.

U.S. Pat. No. 6,197,587 relates to methods of (i) inducing indirect somatic embryogenesis from cacao tissue explants, and (ii) regenerating cacao plants from somatic embryos. Tissue culture media adapted for use in the methods are provided, including primary callus growth medium, secondary callus growth medium, embryo development medium, primary embryo conversion medium, secondary embryo conversion medium, and plant regeneration medium. Although the process of inducing somatic embryos in cacao explants may be carried out in the dark or under light, darkness is preferred.

U.S. Pat. No. 5,312,801 relates to a method for regeneration of somatic embryos from non-zygotic or zygotic tissue, and provides a means for regeneration of cacao plantlets and plants from somatic embryos. Although it is indicated that somatic embryos may be derived from any source, the focus is on the use of nucellus and young flower bud petals. The methods are carried out in low light (300-100 lux, which is equivalent to 5.76-1.95 μmol/m$^2$/sec) or in darkness.

DE 102010044562 A1 relates to automated techniques for in vitro propagation of plants based on somatic embryogenesis, and a process for forming homogenous plant clusters based on a regeneration technique using stem cells from the apical meristem. The resulting directed proliferation under targeted expression of phytohormones leads to formation of homogenous secondary embryoids with unlimited proliferation ability. A nutrient medium having a composition that is adjusted to induce defined differentiation is provided for controllable plant regeneration. The methods are carried out using small explants taken from meristematic material.

The article by Vinterhalter relates to direct somatic embryogenesis in celandine (*Chelidonium majus* L.) using whole epicotyls explants of seedlings after prolonged cultivation on MS medium, with or without plant growth regulators. Somatic embryos developed into plantlets, which entered additional cycles of somatic embryogenesis. Embryos that developed into rooted plantlets could be acclimated in a greenhouse.

The article by Iantcheva relates to a procedure for direct somatic embryogenesis from wild *Medicago* spp. using various explants, including meristematic zones (hypocotyls, cotyledons, and petiole bases from seeds). Solid medium supplemented with thidiazuron or 6-benzylaminopurine at different concentrations promoted the process. Secondary embryogenesis was also observed. Cuttings of clusters of primary and secondary embryos were used for cyclic production of new embryo generations. Regenerated plants with well-developed root systems on medium with reduced levels of macroelements and sucrose were adapted to a greenhouse.

The article by Guiltinan relates to a procedure for the stimulation of somatic embryogenesis and plant regeneration from non-zygotic somatic tissues of cacao, involving the use of several culture steps in combination with the use of the synthetic cytokinin thidiazuron (TDZ) and a synthetic auxin (2,4D). Three steps are used, including callus induction, embryo development, and plant regeneration. When used in the process, 100% of explants taken from staminodes and 60% of explants taken from petal bases produced somatic embryos, and up to 37% of the selected mature somatic embryos produced were capable of conversion into plantlets.

In contrast to the indirect somatic embryogenesis methods described in the prior art, the present invention beneficially provides methods for producing embryos using techniques that include direct somatic embryogenesis. Accordingly, the methods of the invention beneficially provide a unique opportunity for tree breeders and cocoa researchers to improve genetic uniformity in plants for use in further testing, and/or improve yields and disease resistance in trees grown for use in cocoa production.

SUMMARY OF THE INVENTION

The present invention meets the unmet needs of the art, as well as others, by providing methods for propagating *Theobroma cacao* in vitro. The methods are particularly useful for the in vitro multiplication of direct somatic embryos (DSEs) or indirect somatic embryos (ISEs) using direct somatic embryogenesis, and plant regeneration. Plants, plants bearing fruit, and plant materials obtained using the methods are also provided. Methods for processing the fruit of the plants to generate cocoa products, particularly edible cocoa products.

According to one aspect, a process for propagating *Theobroma cacao* is provided, which may include the following steps:

(a-1) obtaining *Theobroma cacao* L. explant material, followed by
  (i) placing the explant material in an induction medium with exposure to light for a period sufficient to obtain primary embryos; and
  (ii) optionally transferring the primary embryos from (i) into a development medium and culturing them with exposure to light for a period sufficient to produce primary embryos by direct somatic embryogenesis;

(b-1) removing tissue of primary embryos, preferably epicotyls of primary embryos obtained after step (a-1), and optionally cutting them into pieces, followed by
  (i) placing the tissue into an induction medium with exposure to light for a period sufficient to obtain secondary embryos; and
  (ii) optionally transferring the secondary embryos from (i) into a development medium and culturing them with exposure to light for a period sufficient to produce secondary embryos by direct somatic embryogenesis;

(c) transferring the secondary embryos from step (b-1) to a medium configured to cause maturation of the secondary embryos.

In an additional aspect, a process for propagating *Theobroma cacao* L. is provided, which may include the following steps:

(a-2) obtaining *Theobroma cacao* L. explant material;
  (i) placing the explant material into a callus formation medium in the dark for a period sufficient to obtain callus formation; and
  (ii) transferring the callus from 1) into an embryo development medium and culturing in the dark for a period sufficient to produce primary embryos by indirect somatic embryogenesis;

(b-2) removing tissue of primary embryos and optionally cutting it into pieces;
  (i) placing the tissue into an induction medium with exposure to light for a period sufficient to obtain secondary embryos; and
  (ii) optionally transferring the secondary embryos from (i) into a development medium and culturing them with exposure to light for a period sufficient to produce secondary embryos by direct somatic embryogenesis;
(c) transferring the secondary embryos from step (b-2) to a medium configured to cause maturation of the secondary embryos.

In additional aspects, a process for propagating *Theobroma cacao* L. is provided in which embryos obtained through the propagation methods are pre-germinated, optionally germinated, and developed into plantlets.

Another aspect relates to a process for preparing direct secondary somatic embryos of *Theobroma cacao* by a method including culturing explants of primary somatic embryos in induction media comprising BAP, followed by developing embryos in development media comprising gibberellic acid. Media for use in such a process are also provided. Preferably, the induction and development media also include sugar.

Other features and advantages of the present invention will become apparent to those skilled in the art upon examination of the following or upon learning by practice of the invention.

BRIEF DESCRIPTION OF THE DRAWINGS

FIG. 6A shows direct somatic embryos after 40 days in induction medium exposed to light (in globular and heart stage). FIG. 6B shows a cross section of cotyledons from a direct somatic embryo in the globular stage. FIG. 6C shows a cross section of a cotyledon with a direct somatic embryo in the heart stage.

DETAILED DESCRIPTION OF THE INVENTION

Figure 1:
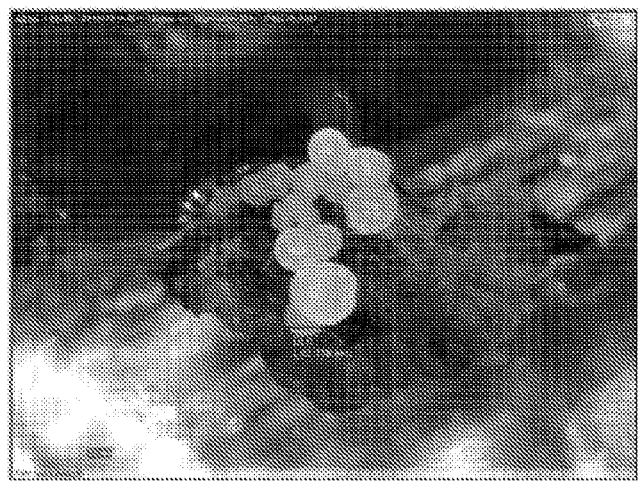
FIG. 1 is a photograph of direct somatic embryos in globular stage from primary somatic embryo epicotyls, which were treated with 1.0 mg/l BAP and 40 g/l sucrose.

The present invention relates generally to methods for propagating *Theobroma cacao* in vitro, and particularly to methods for the in vitro multiplication of direct somatic embryos (DSEs) and indirect somatic embryos (ISEs) using direct somatic embryogenesis, followed by plant regeneration, as well as plants, plants bearing fruit, and plant materials that may be obtained by the methods. Methods for processing the fruit of the plants to generate cocoa products, particularly edible cocoa products, are also provided.

Direct somatic embryogenesis is a morphological event in which somatic embryos originate directly from the plant's tissue matrix, without the formation of callus as an intermediate stage. This is the key difference between direct and indirect somatic embryogenesis: indirect somatic embryogenesis requires callus formation. Another difference between these types of regeneration is the response to the action of growth regulators. Whereas direct somatic embryogenesis is generally characterized by the cultivation of a single culture medium with the addition of just a cytokinin or another stressor agent, indirect somatic embryogenesis is generally characterized as requiring a high auxin concentration or specific ratios of auxin/cytokinin for callus formation in an initial culture medium. After callus is formed, another medium having no auxin or a lower concentration of auxin is used during subsequent transfers, as compared to the medium used for embryogenic callus induction.

The methods described herein, and the somatic embryos, plantlets, plants, and other plant materials disclosed herein are based in part on the surprising discovery that it is possible to induce direct somatic embryogenesis in liquid or solid media via methods that may include exposing the explant material to light.

The methods of the invention improve the propagation process by permitting the production of embryos with reduced callus formation, and in some aspects without the formation of any embryogenic callus, thereby providing a way of obtaining a large number of normal embryos in a short time, as compared with indirect somatic embryogenesis procedures. In some aspects, the plant used to initiate somatic embryogenesis is *Theobroma cacao* (cacao), most preferably *Theobroma cacao* L. Development of mature *Theobroma* spp. using primary somatic embryogenesis starting from vegetative plant explants has not previously been achieved.

According to one aspect, a process for propagating *Theobroma cacao* is provided, the process comprising carrying out the following steps:
(a-1) obtaining *Theobroma cacao* L. explant material, followed by
  (i) placing the explant material into an induction medium with exposure to light for a period sufficient to obtain primary embryos; and
  (ii) optionally transferring the primary embryos from (i) into a development medium and culturing them with exposure to light for a period sufficient to produce primary embryos by direct somatic embryogenesis;
(b-1) removing tissue of primary embryos, preferably epicotyls of primary embryos obtained after step (a-1), and optionally cutting it into pieces, followed by
  (i) placing the tissue into an induction medium with exposure to light for a period sufficient to obtain secondary embryos; and
  (ii) optionally transferring the secondary embryos from (i) into a development medium and culturing them with exposure to light for a period sufficient to produce secondary embryos by direct somatic embryogenesis;
(c) transferring the secondary embryos from step (b-1) to a medium capable of causing maturation and pre-germination of direct secondary embryos into plants, culturing the secondary embryos in said medium for a period sufficient to allow maturation, pre-germination and optionally also germination of said secondary embryos in said medium, and (d) developing plantlets from the pre-germinated or germinated secondary embryos obtained in step (c).

By conducting the process using direct somatic embryogenesis throughout stages (a-1) and (b-1), the problems associated with the use of undifferentiated callus material as discussed above are avoided. Although it may be possible to utilize the torpedo embryos attained in step (a-1)(i) in order to provide source material for development of secondary embryos, in the case of Theobroma cacao L., it has been discovered that epicotyl material derived from primary embryos subjected to step (a-1)(ii) provides a convenient source of explant material for the development of secondary embryos. Furthermore, contrary to many of the previously described processes, it has been discovered that exposure to light during both stages (a-1) and (b-1) leads to an efficient in vitro propagation process.

However, the invention is not to be construed as only being directed to the use of direct primary and secondary somatic embryogenesis. To the contrary, according to another aspect, a process for propagating Theobroma cacao L. is provided, the process comprises carrying out the following steps:

(a-2) obtaining Theobroma cacao L. explant material, followed by
  (i) placing the explant material into a callus formation medium in the dark for a period sufficient to obtain callus formation; and
  (ii) transferring the callus from 1) into an embryo development medium and culturing in the dark for a period sufficient to produce primary embryos by indirect somatic embryogenesis;

(b-2) removing tissue of primary embryos, preferably epicotyls of primary embryos obtained after step (a-2), and optionally cutting them into pieces, followed by
  (i) placing the tissue into an induction medium with exposure to light for a period sufficient to obtain secondary embryos; and
  (ii) optionally transferring the secondary embryos from (i) into a development medium and culturing them with exposure to light for a period sufficient to produce secondary embryos by direct somatic embryogenesis;

(c) transferring the secondary embryos from step (b-2) to a medium capable of causing maturation and pre-germination of direct secondary embryos into plants, culturing the secondary embryos in said medium for a period sufficient to allow maturation, pre-germination and optionally also germination of said secondary embryos in said medium, and (d) developing plantlets from the pre-germinated or germinated secondary embryos obtained in step (c).

By conducting the process using indirect somatic embryogenesis during stage (a-2), preferably with reduced callus formation as compared to existing indirect somatic embryogenesis techniques, and direct somatic embryogenesis during stage (b-2), the higher multiplication of embryos afforded by the use of indirect somatic embryogenesis is beneficially provided, while the use of direct somatic embryogenesis for secondary embryo develop reduces the risk of somaclonal variation in the embryos produced. The epicotyl material derived from the primary indirect embryos subjected of stage (a-2) provides a convenient source of explant material for the development of secondary embryos. Furthermore, contrary to many of the previously described processes, it has been discovered that exposure to light during stage (b-2) leads to an efficient in vitro propagation process.

Suitable explant material for use in step (a-1) or (a-2) of the process of the invention may include, but is not limited to petals, staminodes, and ovales.

The culture media used in step (a-1) may include induction media, and optionally development media, used in sequence. Each media includes components necessary for the induction and development of primary embryos as understood in the art. Thus, the media may comprise, without limitation, macro and micro salts solution with vitamins, growth hormones, and an energy source such as glucose or sucrose. However, since the process is one of direct somatic embryogenesis, the media does not contain hormones such as 2,4D. The phytohormone 2,4D is known to produce somaclonal variation and a large amount of embryos that cannot be converted into plants. However, one or more plant growth regulators or hormones may be provided in the media, including, for example, ethephon, kinetin, putrescine, spermidine, hydrogen peroxide, 6-(γ,γ-dimethylallylamino)purine (2iP), and gibberellic acid/gibberellin The plant growth regulators or hormones may be provided in amounts capable of supporting direct somatic embryogenesis, for example, 0.01 mg/L, 0.05 mg/L, 0.10 mg/L, 0.20 mg/L, 0.30 mg/L, 0.50 mg/L, 0.75 mg/L, 1.0 mg/L, 1.25 mg/L, 1.5 mg/L, 1.75 mg/L, 2.0 mg/L, 2.25 mg/L, 2.5 mg/L, 2.75 mg/L, or 3.0 mg/L. In the case of the plant growth hormone kinetin, where provided, it is provided in an amount of from 0.01 mg/ml to 10 mg/ml, preferably 0.1 mg/ml to 1 mg/ml, and more preferably 0.3 mg/ml to 0.5 mg/ml. Particular examples of media that are within the scope of the invention are illustrated below.

For step (a-2), callus formation media and embryo development media are provided. Thus, the media may comprise, without limitation, macro and micro salts solution with vitamins, growth hormones, and an energy source such as glucose or sucrose. According to certain aspects, because the step is based on indirect somatic embryogenesis, the phytohormone 2,4D may be included in the media, for example, in an amount of about 0.50 mg/L to 3.0 mg/L. Preferably, 2,4D is included in an amount of from 1.0 mg/L to 2.0 mg/L. Additional hormones associated with indirect somatic embryogenesis may also be included, such as the synthetic cytokinin thidiazuron (TDZ). TDZ may be included in the media, for example, in an amount from 0.5 µg/L to 10.0 µg/L. Preferably, TDZ is included in an amount from about 2.5 µg/L to 7.5 µg/L. More preferably, TDZ is included in an amount of about 5.0 µg/L.

The primary embryogenesis of step (a-1) or (a-2) is suitably carried out in a container depending upon the nature of the medium used. For example, where the medium is solid, step (a-1) or (a-2) may suitably be carried out in a Petri dish, or where the medium is liquid, the container may comprise an Erlenmeyer flask or a reaction vessel. In the case of reactions carried out in a liquid medium, the container may be subject to agitation during or throughout the culture process.

Step (a-1) or (a-2) is continued for a period sufficient to provide primary embryos suitable for use in step (b-1) or (b-2). According to one aspect, during step (a-1) or (a-2), embryos with developed epicotyls are formed for use in step (b-1) or (b-2), respectively. Typically the development of primary embryos having developed epicotyls is achieved over a period of from 4-16 weeks, preferably 6-14 weeks, more preferably 8-12 weeks. According to some aspects, the primary embryos with developed epicotyls are obtained in about 10 weeks. During the development of the primary embryos, the temperature is maintained in the range of from 20-32° C., preferably from 24-28° C., and more preferably at about 27° C.

In a particular embodiment, step (a-1) may be carried out in two stages, the first stage being effected in a first culture medium specifically adapted to produce embryogenesis induction, and the optional second stage may be carried out in a second culture medium to produce embryogenesis expression and produce embryos.

In other embodiments, step (a-2) is carried out in two stages, the first stage being a callus development stage effected in a callus development medium adapted to cause callus formation, and the second stage is an embryo development stage carried out in a second embryo development medium to cause embryos to develop from the callus.

The salts and plant hormones used in the first culture medium used in step (a-1) may be varied. According to one aspect, the first culture medium may contain one or more growth regulators. In one preferred aspect, the growth regulators include the cytokinin 6-Benzylaminopurine (BAP) and gibberellic acid, which may be used to induce direct somatic embryogenesis. According to a further aspect, a suitable first culture medium includes the following components:

TABLE 1

| Component | Amount |
| --- | --- |
| macro-nutrients MS (Murashige and Skoog, 1962) | 25% |
| Micronutrients | 50% |
| $KH_2PO_4$, | 20.5-80.5 mg/l, e.g. 42.5 mg/l |
| Fe-EDTA, | 5-40.5 mg/l, e.g. 21.5 mg/l |
| pyridoxine, | 0.1-50 mg/l, e.g. 1 mg/l |
| nicotinic acid, | 0.1-50 mg/l, e.g. 1 mg/l |
| Thiamine | 1.0-500 mg/l, e.g. 10 mg/l |
| BAP | 0.1-2.0 mg/l, e.g. 1 mg/l |
| Gibberellic acid | 0.1-2.0 mg/l, e.g. 0.6 mg/L |
| sucrose, | 20-120 g/l, e.g. 30 g/l |
| myo-inositol, | 10-200 mg/l, e.g. 100 mg/l |
| Phytagel (solid media only) | 1.5-2.5 g/l, e.g., 2.0 g/l |

The first stage of step (a-1) may be carried out over a period of from 1-8 weeks, preferably about 2-6 weeks, and more preferably until torpedo-stage embryos are developed from the explant material.

In aspects in which the optional second stage of step (a-1) is carried out, the medium used may also contain a cytokinin, such as BAP, but the concentration is reduced to facilitate embryo differentiation and development of embryos, as well as multiplying the numbers of embryos produced. For example, the medium used in the second stage of step (a-1) may be similar to the medium used in the first stage, but contain BAP at less than half, for example about a third, of that used in the medium used in the first stage of step (a-1). Thus where a typical medium used in the first stage of step (a-1) may contain BAP in an amount of about 1 mg/l, the medium used in the second stage of step (a-1) may contain BAP in an amount of 0.3 mg/l.

This second stage of step (a-1) can be effected for a period for example of from 2 to 12 weeks, preferably until the primary embryos develop epicotyls that may be used as source material for the formation of secondary embryos. During this time, the culture media may require the replenishment on multiple occasions, for example about three or four or more times through the treatment.

Step (a-1) or (a-2) is preferably carried out using explants originating from flower buds. In one aspect, from 1 to 20 explants will be placed in each container being used for the development of embryos, such as a Petri dish or Erlenmeyer flask. For instance, from 2 to 10 flower buds may be placed in a Petri dish of 100×20 mm or a 250 ml Erlenmeyer flask, together with about 25 to 30 ml of media. During step (a-1), a multiplication of embryos, for example with an index of multiplication of from 3-10 embryos per explant, may be observed. During step (a-2), a larger multiplication of embryos, for example with an index of multiplication of from 5-50 embryos per explant may be observed.

At the end of step (a-1) or (a-2), the resultant primary embryos are recovered for use in direct somatic embryogenesis to produce secondary embryos. Preferably, epicotyls are removed from the embryos and cut into small pieces. Typically, each epicotyl is cut into between 4 and 6 pieces to ensure that these pieces are of suitable size for direct somatic embryogenesis. By using multiple pieces of each embryo produced in step (a-1) or (a-2) in step (b-1) or (b-2), the number of secondary somatic embryos obtainable is increased as compared with the number of primary somatic embryos generated.

The procedure of step (b-1) or (b-2) is carried out in light. The photoperiod may range, for example, from 12:12 to 24:0, preferably from 13:11 to 20:4, more preferably from 14:10 to 18:6. A particularly preferred photoperiod is about 16:8, with about 16 hours in the light followed by 8 hours in the dark. Exposure to light can be ensured by positioning the substrates in appropriately-illuminated chambers, as is understood in the art. A photosynthetic active radiation (PAR) or photosynthetic photon flux density (PPFD) of 30-240 µmol/m$^2$·sec may be used, preferably 50-190 µmol/m$^2$·sec. In some aspects, for instance, a photoperiod of 16:8 hours light:dark and a photosynthetic active radiation (PAR) or photosynthetic photon flux density (PPFD) of 50-60 µmol/m$^2$·sec may be used.

Step (b-1) or (b-2) may be carried out in two stages, the first stage being effected in a first culture medium specifically adapted to produce embryogenesis induction, and the optional second stage may be carried out in a second culture medium to produce embryogenesis expression and produce secondary embryos. The media may be either a solid or liquid medium, in a suitable container, which may be a Petri dish or an Erlenmeyer flask as described above.

The culture medium used in step (b-1) or (b-2) is selected to encourage direct somatic embryogenesis. For instance, suitable culture media may comprise the following materials, where the Amino Acid Stock 1000× noted in Table 2 includes L-Lysine 45.65 mg, L-Leucine 32.80 mg, L-Tryptophan 51.05 mg, Arginine 43.55 mg, and Glycine 18.76 mg:

TABLE 2

| Component | Amount |
| --- | --- |
| macro-nutrients MS (Murashige and Skoog, 1962) | 100% |
| Micronutrients | 100% |
| calcium pantothenate | 2.0 mg/l, e.g. 1 mg/l |
| Fe-EDTA, | 10-42.5 mg/l, e.g. 21.5 mg/l |
| pyridoxine, | 0.1-50 mg/l, e.g. 1 mg/l |
| nicotinic acid, | 0.1-50 mg/l, e.g. 1 mg/l |
| Thiamine | 0.1-2.0 mg/l, e.g. 1 mg/l |
| Biotin | 0.1-2.0 mg/l, e.g. 0.1 mg/l |
| BAP | 0.1-2.0 mg/l, e.g. 0.3 mg/l |
| sucrose, | 20-120 g/l, e.g. 30 g/l |
| myo-inositol, | 10-200 mg/l, e.g. 100 mg/l |
| KNO3 | 0.1-3.0 g/l, e.g., 0.3 g/l |

TABLE 2-continued

| Component | Amount |
| --- | --- |
| Phytagel (solid media only) | 1.5-3.0 g/l, e.g., 2.2 g/l |
| Amino Acid Stock Solution 1000X | 1 ml/L |

In aspects in which the optional second stage of step (b-1) or (b-2) is carried out, the medium used may also contain a cytokinin, such as BAP, but the concentration is reduced to facilitate embryo differentiation and development of embryos, as well as multiplying the numbers of embryos produced. BAP may be provided in an amount from 0.1 to 2.0 mg/L, preferably 0.5 to 1.5 mg/L, more preferably about 1.0 mg/L. For example, the medium used in the second stage of step (b-1) or (b-2) may be similar to the medium used in the first stage, but contain BAP at less than half, for example about a third, of that used in the medium used in the first stage of step (b-1) or (b-2). Thus, if a typical medium used in the first stage of step (b-1) may contain BAP in an amount of about 1 mg/l, then the medium used in the second stage of step (b-1) may contain BAP in an amount of 0.3 mg/l.

In certain aspects in which both stages of step (b-1) or (b-2) are carried out, the specific balance between BAP/sucrose in induction medium and gibberellic acid/sucrose in development medium has surprisingly been found to be capable of inducing direct somatic embryogenesis, expression and development of normal embryos, thus promoting direct somatic embryogenesis of *Theobroma cacao*, and particularly *Theobroma cacao* L.

A principal advantage of direct somatic embryogenesis is to obtain normal embryos where the production media does not contain 2,4D. This phytohormone is known to produce somaclonal variation and a large amount of embryos that cannot be converted into plants.

In some aspects of the invention, it has been found that gibberellic acid acts as a stimulator agent for the development of normal embryos having a high capacity to convert into plants, particularly when used in combination with a sugar, such as sucrose, glucose, fructose, mannose, lactose, galactose, etc., and preferably sucrose. The secondary embryo development and maturation process in *Theobroma cacao*, particularly in direct somatic embryogenesis, is affected by concentration of gibberellic acid, and concentration of sucrose. The concentration of gibberellic acid may be from about 0.01 to about 1.0 mg/L, preferably from about 0.2 to about 0.8 mg/L, and most preferably about 0.6 mg/L. The concentration of sucrose may be from about 10 g/L to about 100 g/L, preferably from about 20 g/L to about 80 g/L, and most preferably about 40 g/L. The effect of sucrose in development medium may be due to its action as an osmotic agent that induces maturation in somatic embryos.

According to a presently-preferred aspect, the induction media used in the first stage of step (b-1) or (b-2) that contains 1.0 mg/L BAP as a stressor agent for stimulating the secondary embryogenic response by direct somatic embryogenesis is associated with 40 g/L sucrose. The development media used in the second stage of step (b-1) or (b-2) that contains 0.6 mg/l gibberellic acid is associated with 40 g/L sucrose. The use of this combination of induction and development media surprisingly and beneficially resulted in 83.3% of embryos produced being normal.

Without wishing to be bound by theory, it is believed that the concentration of sugar in an induction medium can be a key factor in switching on/off the specific type of in vitro morphogenic pathway. It is further believed that different stressor agents might induce different morphogenic responses in plant cells, such as inhibition of cell elongation, localized stimulation of cell division, and alteration of the cell differentiation status.

Step (b-1) or (b-2), whether carried out in one or two stages, is carried out for a period sufficient to produce secondary embryos by direct somatic embryogenesis, where the secondary embryos are suitable for use in the development of plants.

The first stage of step (b-1) or (b-2) may be carried out over a period of from 1-4 weeks, for example for about 2 weeks, preferably until torpedo-stage embryos are developed from the explant material, which are then used in the second stage of step (b-1) or (b-2).

When only a single stage is used for step (b-1) or (b-2), the procedure of the first stage of step (b-1) or (b-2) is carried out for a period of from 2-16 weeks, preferably 2-12 weeks, more preferably 4-10 weeks, and most preferably 6-8 weeks, until the secondary embryos develop to a stage sufficient to permit them to be used in further steps toward the development of plants, for example, maturation.

When step (b-1) or (b-2) is carried out in two stages, the second stage can be effected for a period for example of from 2 to 12 weeks, preferably until the secondary embryos develop to a stage sufficient to permit them to be used in further steps toward the development of plants, for example, maturation. During this time, the culture media may require the replenishment on multiple occasions, for example about three or four or more times through the treatment. A suitable time period for step (b-1) or (b-2) may be from 2 to 12 weeks, preferably 4 to 8 weeks, and more preferably from 2 to 6 weeks.

During this time, the temperature is generally maintained within the range of from 23-29° C., preferably from 25-28° C. In some aspects, a temperature of 27° C. is preferred.

The media used in the practice of the invention may be either in liquid or solid form. Solid media typically contains a gelling agent such as phytagel, although any suitable gelling agent may be used in order to provide solid media. According to some aspects, the use of liquid media is preferred because it can result in a shorter overall process for obtaining plantlets. For example, the production of embryos using solid media may take from 12-15 months from the initial production stage (7-8 months), to the maturation stage (1.5-2 months), to the germination stage (1-2 months), to the conversion stage (2-3 months). The production of embryos using primarily liquid media may take only from 8 to 11 months, from the initial production stage (6-7 months), to the maturation stage (1-1.5 months), to the germination stage (1-1.5 months), to the conversion stage (1-2 months).

The expression 'with exposure to light' as used herein refers to protocols and methods wherein the substrates are exposed to light for at least part of each 24 hour period. In particular the substrates are exposed to light for at least 50% of each 24 hour period, day and preferably more than this. The photoperiod may range, for example, from 12:12 to 24:0, preferably from 13:11 to 20:4, more preferably from 14:10 to 18:6. A particularly preferred photoperiod is about 16:8, with about 16 hours in the light followed by 8 hours in the dark. Exposure to light can be ensured by positioning the substrates in appropriately-illuminated chambers, as is understood in the art. In a particular embodiment, a photosynthetic active radiation (PAR) or photosynthetic photon flux density (PPFD) of 30-80 $\mu$mol/m$^2$·sec, preferably 40-70 $\mu$mol/m$^2$·sec, and more preferably 50-60 $\mu$mol/m$^2$·sec is used.

In a particularly preferred embodiment, a further step may be carried out after step (b-1) or (b-2) above, but before step (c). This optional additional step, referred to herein as step (b-3), is one in which the number of secondary embryos produced is multiplied further. This is effected by initiating the expression and production of new direct secondary somatic embryos from explant material taken from the secondary embryos produced in step (b-1)(i) or (b-2)(i) and optionally (b-1)(ii) or (b-2)(ii). The products of step (b-1) or (b-2) are transferred to a suitable liquid or solid culture medium, which may be similar to that used in the step (a-1)(ii) or (a-2)(ii), in a suitable container as described above. The embryos are then cultured at a temperature of from 23-29° C., for instance from 25-28° C. with exposure to light as described above. Once again, a photoperiod of 16:8 hours with 50-60 μmol/m$^2$·sec is preferred. This step (b-3) may optionally be continued until a suitable multiplication of embryos has been achieved. A suitable index of multiplication of embryos at this stage may be in the range of 5-19 embryos per epicotyl explant. This may generally be achieved in a period of from 5-10 weeks, for example, from 6-10 or 8-10 weeks. During step (b-3), the medium is changed at least once, and may be changed 3, 4, or more times during this step.

In some aspects, when step (b-3) is carried out in liquid medium in an Erlenmeyer flask, this will have a capacity of 250 ml and is suitably agitated throughout the procedure, for example, on a shaker at 100 revolutions per minute (rpm).

Thus the process of the present invention, by utilizing direct somatic embryogenesis in steps (b-1), (b-2), and (b-3) (where used), provides the production of a large number of normal embryos and plantlets in a relatively short time.

The treatment of the direct secondary embryos in step (c) to produce maturation and pre-germination, and optionally also germination and conversion of embryos into plants, is suitably carried out in a liquid medium. The medium may be held in any suitable container, although a temporary immersion system (TIS) reactor or in Petri dish in solid medium are preferred aspects. Incubation is suitably effected at a temperature of from 23-29° C., for example from 25-28° C. While maturation is suitably effected in the dark, pre-germination and germination steps are carried out with exposure to light as described above. Again a photoperiod of 16:8 hours with 50-60 μmol/m$^2$·sec may be suitable.

Incubation is continued for a period sufficient to allow maturation, pre-germination and optionally also germination of said secondary embryos in said medium. The medium in this case will be designed to allow these processes to proceed. A typical medium may comprise the following components, where the Amino Acid Stock 1000× noted in Table 2 includes L-Lysine 45.65 mg, L-Leucine 32.80 mg, L-Tryptophan 51.05 mg, Arginine 43.55 mg, and Glycine 18.76 mg:

TABLE 3

| Component | Amount |
| --- | --- |
| macro-nutrients MS (Murashige and Skoog, 1962) | 50%-100% |
| Micronutrients | 50%-100% |
| calcium pantothenate | 0.1-2.0 mg/l, e.g. 1 mg/l |
| Fe-EDTA, | 10-100 mg/l, e.g. 43 mg/l |
| pyridoxine, | 0.1-50 mg/l, e.g. 1 mg/l |
| nicotinic acid, | 0.1-50 mg/l, e.g. 1 mg/l |
| Thiamine | 0.1-500 mg/l, e.g. 1 mg/l |
| Biotin | 0.1-2.0 mg/l, e.g. 0.1 mg/l |
| sucrose, | 20-120 g/l, e.g. 40 g/l |
| myo-inositol, | 10-200 mg/l, e.g. 100 mg/l |
| KNO$_3$ | 0.1-3.0 g/l, e.g., 0.3 g/l |
| Amino Acid Stock 1000X | 1 ml/l |

In general, this will be complete within a period of from 6-10 weeks, for example from 8-10 weeks. Suitably, the medium will be changed on a number of occasions during this treatment, for example from 3-8 times during step (c).

The pre-germinated or germinated secondary embryos obtained in step (c) can then be developed into plantlets using conventional methods. For example, the in vitro generated materials are transplanted in the nursery for acclimatization in a culture substrate which has a mixture of components as perlite, coconut peat, soil, etc. for example. Subsequently, the plants may be transplanted in the field and grown into cocoa trees, and in preferred aspects, the plants bear fruit that may be further processed to provide cocoa products.

All in all, the process of the invention may be carried out over a period of from 22 weeks to one year, preferably from 22-36 weeks, from in vitro induction to greenhouse.

Additional advantages may be achieved using the process of the invention. The organization of the steps allows for improvement in the synchronization of the occurrence and development of the embryos. Furthermore, maturation, pre-germination, germination and conversion of embryos into plants can, if required, be effected in a TIS bioreactor, thus allowing the plant propagation process to be carried out simply and with greater efficiency. The use of such bioreactors makes the process amenable to automation and provides for cost and labor savings due to factors such as the reduced need for manual steps and the use of gelling agents.

According to one aspect in which a bioreactor is used to carry out maturation, pre-germination, germination, and conversion of embryos into plants, the direct secondary somatic embryos obtained by the methods described herein may be transferred into TIS bioreactor containing liquid medium. The medium may include, for example, macro-nutrients MS (Murashige and Skoog, 1962) 50%, micro-nutrients MS 50%, supplemented with 43 mg/l Fe-EDTA, 1 mg/l pyridoxine, 1 mg/l nicotinic acid, 1 mg/l thiamine, 1 mg/l calcium pantothenate, 0.01 mg/l biotin, 100 mg/l myo-inositol, 40 g/l sucrose and was of pH 5.8. However, other suitable media may be substituted for use in the bioreactor. After a period in the bioreactor of from 2-10 weeks, preferably 4-8 weeks, in the dark at a temperature of from 25-30° C., preferably 27° C., to allow for maturation, the contents are cultured in the bioreactor in the light. The culturing in light preferably uses a photoperiod of 16:8 hours at 50-60 μmol/m$^2$·sec, although other photoperiods may be used as described above. The culturing in light is carried out at a temperature of from 25-30° C., preferably 27° C., for a period of from 6 to 14 weeks, preferably 8-12 weeks, and more preferably about 10 weeks. Medium should be changed at regular intervals during the treatment, such as 2, 3, 4, or more changes. During this time, the embryos undergo pre-germination, and germination. Preferably, the germinated secondary embryos obtained at the end of this process are suitable for transplantation into the greenhouse.

In addition to the methods for propagating Theobroma cacao described herein, methods for removing the fruit is removed from the plant and processing it into a cocoa product are also provided. The processing techniques used to prepare cocoa products include partially or fully depulping the fruit, fermenting the partially or fully depulped fruit using microbiological processes or chemical processes, drying the fruit by exposing it the sun or an artificial dryer, including, but not limited to, a Samoan dryer, Buttner dryer, and a platform dryer.

According to some aspects the fruit may be further roasted and winnowed to generate a nib that is converted to cocoa liquor or cocoa butter. The nib or cocoa liquor may be converted to cocoa powder. The liquor, cocoa butter, and nib may be mixed with sugar or other natural or synthetic sweetening substances. In some aspects, the resulting mixture may be in the form of a paste.

The paste may be refined, optionally by means of a roller system, in order to generate smaller particle sizes within the paste. According to further aspects, milk solids may be added, and the mixture then further processed to a milk crumb. This mixture may be mixed in a conche, optionally with cocoa butter and emulsifier. The paste and crumb may also be mixed with cocoa butter and emulsifier in a conche. The conche used for the mixing includes, but is not limited to, a Frissee conch, a Tourell conche, Macintyre refiner/conche, and a wiener process.

The end product of this process of preparing, and optionally refining and further processing the paste is an edible cocoa containing product, including, but not limited to, chocolate, compound chocolate, or a chocolate-like substance.

Presently-preferred cocoa products that may be produced using the fruit from the plants propagated include cocoa liquor, chocolate, compound chocolate, chocolate-like substance, cocoa powder, and cocoa butter. Cocoa-containing products obtained by the processes described above are also provided.

EXAMPLES

The invention will now be particularly described by way of example. However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

Example 1—Primary Somatic Embryogenesis (modified from the protocol of Guiltinan et al., 1997)
Materials
Chemicals from Sigma Chemical Co., St. Louis, Mo. were used for all media preparation. Medium pH was adjusted using 1N KOH, prior to autoclaving. All media were autoclaved for 20 min at 121° C. A powdered form of the DKW medium developed by Driver and Kuniyuki (1984) and Tulecke and McGranahan (1985) can be obtained from Sigma Chemical Co. (D-6162). However, due to the hygroscopic nature of the powdered preparation, the use of stock solutions containing the chemical components of the DKW medium is recommended for medium preparation. A hydrated powdered mixture often becomes difficult to dissolve in water, and thus may reduce the effectiveness of the medium. Macronutrients in the DKW medium were separated into A and B stock solutions in order to avoid chemical interactions between inorganic salts at high concentrations, and to prevent precipitation of salts during storage. Fresh stock solutions of growth regulators including TDZ and 2,4D; were made every 3 months. Calcium hypochlorite [$Ca(OCl)_2$] was obtained from Aldrich Chemical Company, Inc. (Milwaukee. Wis.)

TDZ solution (0.5 mg/ml): dissolve 5 mg thidiazuron (Sigma P-6186) in 100 µl of 1N KOH and add $dH_2O$ to a final volume of 10 ml. Store at 4° C.

2,4D solution (10 mg/ml): dissolve 100 mg 2,4-dichlorophenoxyacetic (Sigma D-8407) in 8 ml of 100% ethanol, and then add $H_2O$ to 10 ml. Store at 4° C.

Kinetin and BAP solution (10 mg/ml): dissolve 10 mg kinetin or BAP in 50 µl 1 N NaOH and add $H_2O$ to 1 ml. Store at −20° C.

DKW 10× macro solution A (per liter): 14.16 g $NH_4NO_3$; 19.68 g $Ca(NO_3)_2$ $4H_2O$. Store at 4° C.

DKW 10× macro solution B (per liter): 15.59 g $K_2SO_4$; 7.40 g $MgSO_4$ $7H_2O$; 1.49 g $CaCl_2$ $2H_2O$; 2.65 g $KH_2PO_4$. Store at 4° C.

DKW 100× micro solution C (per liter): 1.70 g $Zn(NO_3)_2$ $6H_2O$; 3.34 g $MnSO_4H_2O$; 3.38 g $FeSO_4$ $7H_2O$; 4.54 g Na-EDTA; 0.48 g $H_3BO_3$; 25 mg $CuSO_4.5H_2O$; 39 mg $Na_2MoO_4.2H_2O$. Store at 4° C.

DKW 1000× vitamin solution (per 100 ml): 10.0 g myo-inositol; 0.2 g thiamin-HCl; 1 g nicotinic acid; 1 g glycine; 1 g tryptophan. Distribute 1 ml aliquot to Eppendorf tube. Store −20° C.

Primary callus growth (PCG) medium (per liter): 100 ml each of DKW solutions A and B; 10.0 ml DKW micro solution; 1 ml DKW vitamin solution; 20.0 g glucose; 250 mg glutamine; 100 mg (=200 mg/L) myo-inositol; 200.0 µl (=2.0 mg/L) 2.4-D solution; 10.0 µl (=5 µg/L) TDZ solution. Adjust pH to 5.8. 2.0 g phytagel (sigma P-8169).

Secondary callus growth (SCG) medium (per liter): 2.3 g McCown's (Lloyd and McCown. 1981) woody plant salt mixture (Sigma M-6774); 1 ml Gamborg's (Gamborg's. 1966) vitamin solution (Sigma G-1019); 20.0 g glucose; 200.0 µl (=2.0 mg/L) 2.4-D solution; 5.0 µl (=0.05 mg/L) BAP solution; or 30.0 µl (=0.3 mg/ml) Kinetin solution. Adjust pH to 5.8. 2.2 g phytagel.

Embryo development (ED) medium (per liter): 100.0 ml each of DKW macro solutions A and B; 10.0 ml DKW micro solution; 1 ml DKW vitamin solution; 40.0 g sucrose. Adjust pH to 5.8. 2.0 g phytagel.

Embryo development (ED) medium (per liter): 100.0 ml each of DKW macro solutions A and B; 10.0 ml DKW micro solution; 1 ml DKW vitamin solution; 30.0 g sucrose; 2.0 g phytagel. Adjust pH to 5.8

Embryo development (EDL) medium (per liter): 100.0 ml each of DKW macro solutions A and B; 10.0 ml DKW micro solution; 1.0 ml DKW vitamin solution; 20.0 g glucose; 0.3 g $KNO_3$; 1.8 g Phytagel. Adjust pH to 5.8

Amino Acid Stock Solution 1000× (1 ml/L each): L-Lysine 45.65 mg/L; L-Leucine 32.80 mg/L; L-Tryptophan 51.05 mg/L; Arginine 43.55 mg/L; Glycine 18.76 mg/L;

Plant regeneration (PR) medium (per liter): 50 ml each of DKW macro solutions A and B; 5 ml DKW micro solution; 0.5 ml DKW vitamin solution; 4.5 mg/l IBA; 10.0 g glucose; 5.0 g sucrose; 0.3 g $KNO_3$. Adjust pH to 5.8. 1.8 g phytagel.

Other solutions: 95% (v/V) ethanol prepared with sterile $H_2O$.

Equipment: Laminar flow hood, dark incubation area with a constant temperature at 25±2° C. and light incubation area with daily cycle of 16 h (light) photoperiod (50-190 μmol m$^{-2}$ s$^{-1}$).

Supplies: sterile 50 ml conical-bottom centrifuge tubes, sterile 100×15 mm Petri dishes, G7 magenta vessels, Pyrex brand laboratory bottles (1 and 0.5 liter), No. 11 scalpel blades with handle, micro forceps, low—temperature electric tape, sterile paper towels and Metro—mix 300 soil mixture (Scotts Sierra Horticultural Product Co. Marylandsville. Ohio)

Plant materials: Unopened 5 to 8 mm in immature cacao flower buds (varies with genotype), collected between 8 am and 11 am in the morning.

Procedure

Staminodes and petals base tissues were used as culture explants. Although immature flower buds with a range of sizes can be collected, large flower buds should be chosen since such flower buds are easier to dissect and handle in the absence of a dissecting microscope. In addition, staminodes and petal base explants should be separated from associated floral parts such as stamen filaments and petal tissue, in order to minimize possible interactions that may affect the in vitro growth of explants.

Collection of immature flower buds in a 50 ml centrifuge tube containing cold water was carried out in the morning before 9:00 am.

Prepare 1% (w/v) calcium hypochlorite solution by dissolving 0.5 g Ca(OCL)$_3$ in 50 ml sterile water in a sterile 50 ml centrifuge tube.

Inside the transfer hood, decant the cold water from the centrifuge tube containing the immature flower buds and transfer all the flower buds into the sterile centrifuge tube containing the calcium hypochlorite solution.

Immerse flower buds in the calcium hypochlorite solution for 20 min. Remove all the solution and add 40 ml sterile water to rinse flower buds. Rinse at least 3 times.

Transfer flower buds to a Petri dish, and cover the plate to prevent desiccation.

Dissection of Flower Bud and Callus Induction

Place two to three layers of sterile paper towels in the transfer hood. Blot dry 4 flower buds on the top surface of the paper towels, and then transfer then onto a Petri dish cover.

Slice the flower buds across at a position of about ⅓ of the flower length from the base using a sterile scalpel blade. Extract staminodes and petal base tissues together from the part of the flower bud using a pair of sterile forceps. Remove any attached petal tissue from the petal base explants.

Transfer staminodes and petal base explants from 4 flower buds into a Petri dish containing 30 ml of PCG medium. Separate any fused staminodes and petal base explants and distribute explants evenly across the medium.

Seal the Petri dishes with double layers of parafilm and maintain cultures in the dark at 25±2° C. for 14 days.

Transfer the staminodes explants to a Petri dish containing 30 ml of SCG medium, and the petal base explants to another identical Petri dish. Seal the dishes and maintain culture in the dark for another 14 days.

Somatic Embryo Expression and Maintenance

Transfer staminodes and petal base explants to Petri dishes containing 30 ml of ED4 medium culture explants in the dark for 14 days.

Subculture explants onto fresh ED3 medium 3-5 times. Maintain embryo cultures in the dark with a subculture interval of 14 days until somatic embryos reach maturity.

Secondary Somatic Embryogenesis Process

Take epicotyls of primary embryos with 10-40 mg of weigh up and cut in pieces, and place in a Petri dish with 30 ml of SCG medium (with BAP or Kinetin depending on the specific genotype) or in flask with 25 ml of SCG liquid medium per 14 days in the light with photoperiod 16 h light:8 h darkness. Put the flasks in a shaker at 100 rpm to incubation in temperature 25-30° C.

Transfer the pieces to a Petri dish containing 30 ml of ED4 medium culture or in flask with 25 ml of ED3 liquid medium per 14 days in the light with photoperiod 16 h light:08 h darkness. Put the flasks in a shaker with 100 rpm for incubation in temperature 25-30° C.

Subculture explants onto Petri dish containing 30 ml fresh ED3 solid medium or in flask with 50 ml of ED3 liquid medium per 14 days in the light with photoperiod 16 h light:08 h darkness. Put the flasks in a shaker with 100 rpm for incubation in temperature 25-30° C.

Transfer the embryos in heart or early torpedo stage and put in bioreactor with a concentration of 10-40 mg/ml of ED3 liquid medium with temporary immersion 6 times a day with 2 minutes per immersion and change the liquid medium every 20-30 days (1 or 2 times). Incubation in 25-30° C. with photoperiod 12 h light:12 h darkness.

Embryo Conversion and Plant Establishment in Liquid Medium

In this period the embryos are maturated and it is necessary to change the medium to EDL liquid medium (concentration 100 mg/ml) with temporary immersion 6 or 8 times a day, with 2 or 1 minutes per immersion, and change the liquid medium every 20-30 days (1 or 2 times) until the embryos have radicals and 3-5 leaves. Then transfer to a greenhouse for acclimatization. Incubate at 25-30° C. with a photoperiod of 12 h light:12 h darkness.

For type I embryos, select germinated embryos and transfer them onto Petri dishes containing 30 ml PR medium.

Maintain cultures under light with a 24-h photoperiod 14 days.

Transfer the embryos that turn green with roots and shoots to PR medium in Magenta vessel.

Maintain cultures as described in steps 15 with subculture into fresh PR medium every 14 days.

Transplant plantlets with developing green leaves and healthy taproots into 4-inch plastic pots containing sterile Metro-Mix 300 soil mixture. Pour water into pot to saturate the soil mixture. Cover the plantlet using a Magenta vessel. Maintain plants in the greenhouse with an 80% humidity controlled by an automatic misting system. Add water regularly to maintain an adequate moisture content for optimal plant growth.

When the plant produces new leaves, remove the cover vessel. Apply a regular amount of fertilizers to enhance plant growth.

Explants should be subcultured to fresh medium every two weeks. Growth reduction, senescence, and tissue browning may occur with subculture intervals longer than 14 days.

Two types of somatic embryos can be identified based on the following characteristics: Type I embryos axis. During extended culture on ED medium, mature Type I embryos tend to remain dormant. After transfer to EDL medium, these embryos show extensive cotyledonary growth, followed by the development of true leaves. Root development in germinating Type I embryos is normally slow. Type II somatic embryos are whitish in color and have a defined embryonic axis structure. These embryos undergo spontaneous germination upon reaching maturity on ED medium. After transfer to EDL medium, these embryos turn green quickly, exhibit a significant hypocotyl elongation, and produce a strong taproot, within a short period of time. Epicotyl and production of true leaves often occur 2 to 3 weeks after transfer.

Example 2—Use of Epicotyls for Induction and Expression of Embryos by Direct Somatic Embryogenesis, and Production of Embryos in Mature Cotyledon Stage Primary Somatic Embryo Development Primary somatic embryos were obtained using the methodology described by Li et al. (1998). All of the reagents used in this experiment are Sigma brand.

Collect immature flower buds of *Theobroma cacao* L. from CCN-10 clones in a 50-ml centrifuge tube containing cold water in the morning before 9:00 am.

Prepare 1% (w/v) calcium hypochlorite solution by dissolving 0.5 g $Ca(OCL)_3$ in 50 ml sterile water in a sterile 50 ml centrifuge tube.

Inside the transfer hood, decant the cold water from the centrifuge tube containing the immature flower buds and transfer all the flower buds into the sterile centrifuge tube containing the calcium hypochlorite solution.

Immerse flower buds in the calcium hypochlorite solution for 25 min. Remove all the solution and add 40 ml sterile water to rinse flower buds. Rinse at least 3 times. Transfer flower buds to a Petri dish, and cover the plate to prevent desiccation.

Place two to three layers of sterile paper towels in the transfer hood. Blot dry 4 flower buds on the top surface of the paper towels, and then transfer then onto a Petri dish cover.

Slice the flower buds across at a position of about ⅓ of the flower length from the base using a sterile scalpel blade. Extract staminodes and petal base tissues together from the part of the flower bud using a pair of sterile forceps. Remove any attached petal tissue from the petal base explants.

Transfer the staminodes and petal base explants to a Petri dish containing 30 ml of PCG medium. Seal the dishes and maintain culture in the dark for 14 days, after, follow with the transferences to SCG medium per 14 days, after this culture period, transfer the explant in ED4 medium per 14 days and then to ED3 medium for expression of embryos for three or four times from 14 days. Seal the Petri dishes with double layers of parafilm and maintain cultures in the dark at 25±2° C. Table 4 compares the components of different media used in the production of primary embryos.

TABLE 4

Composition of PCG, SCG, ED4 and ED3 medium
PRIMARY SOMATIC EMBRYOGENESIS MEDIUMS BY INDIRECT VIA

| PCG MEDIUM | 1 L | SCG MEDIUM | 1 L |
| --- | --- | --- | --- |
| DKW Macro A (10X) | 100 mL | McCown's WPM (Macro) | 100% |
| DKW Macro B (10X) | 100 mL | McCown's WPM (Micro) | 100% |
| DKW Micro (100X) | 10 mL | | |
| DKW Vitamins (1000X) | 1 mL | Gamborg BS Vitamins (1000X) | 1 mL |
| Glucose | 20 g | Glucose | 20 g |
| 2,4-D (1 mg/mL) | 2000 µL | 2,4-D (1 mg/mL) | 2000 µL |
| TDI (1 mg/mL) | 25 µL | 6-BAP (1 mg/mL) | 50 µL |
| | | or | or |
| | | Kinetin (1 mg/mL) | 300 µL |
| Glutamine | 250 mg | | |
| Myo-Inositol | 100 mg | | |
| pH to 5.8 with 1M KOH | | pH to 5.8 with 1M KOH | |
| Phylagel | 2 g | Phylagel | 2.2 g |
| Autoclave | 18 minutes | Autoclave | 18 minutes |
| CD-4 | 1 L | CD-3 | 1 L |
| DKW Macro A (10X) | 100 mL | DKW Macro A (10X) | 100 mL |
| DKW Macro B (10X) | 100 mL | DKW Macro B (10X) | 100 mL |
| DKW Micro (100X) | 10 mL | DKW Micro (100X) | 10 mL |
| DKW Vitamins (1000X) | 1 mL | DKW Vitamins (1000X) | 1 mL |
| Sucrose | 40 g | Sucrose | 30 g |
| pH to 5.8 with 1M KOH | | pH to 5.8 with 1M KOH | |
| Phylagel | 2 g | Phylagel | 2 g |
| Autoclave | 18 minutes | Autoclave | 18 minutes |

For the production of secondary embryos, epicotyls are taken from primary somatic embryos with size 1 cm and 40 mg of weight and they were cut in 10-15 pieces and placed into flask with 25 ml of liquid medium for embryogenic induction (Table 5) with some modifications in the experimental design (Table 7) per 5 weeks (step c). The culture is exposed to a light:dark 16:8 photoperiod, at a temperature of 27±2° C. and photosynthetic active radiation (PAR) or photosynthetic photon flux density (PPFD) of 50-190 µmol/$m^2$ per second.

After this period, the somatic embryos in globular stage are transferred into the Petri dish in semi-solid developing media (Table 6) with some modifications (Table 8), with a 21-day culture period in light conditions until the embryos express and develop to the heart or early torpedo stage.

Afterward, the cultures were transferred into the Petri dish in the same medium, but without gibberellic acid and with the same culture conditions but in the dark with transferences every 14 days for embryo's maturation.

TABLE 5

Induction media

| Component | Amount |
|---|---|
| macro-nutrients MS (Murashige and Skoog, 1962) | 25% |
| Micronutrients | 50% |
| $KH_2PO_4$, | 20.5-80.5 mg/l e.g. 42.5 mg/l |
| Fe-EDTA, | 5-40.5 mg/l e.g. 21.5 mg/l |
| pyridoxine, | 0.1-50 mg/l e.g. 1 mg/l |
| nicotinic acid, | 0.1-50 mg/l e.g. 1 mg/l |
| Thiamine | 1.0-500 mg/l e.g. 10 mg/l |
| BAP | 0.1-2.0 mg/l e.g. 1 mg/l |
| sucrose, | 20-120 g/l e.g. 30 g/l |
| myo-inositol, | 10-200 mg/l e.g. 100 mg/l |
| Phytagel (solid media only) | 1.5-2.5 g/l e.g., 2.0 g/l |

TABLE 6

Development medium

| Component | Amount |
|---|---|
| macro-nutrients MS (Murashige and Skoog, 1962) | 100% |
| Micronutrients | 100% |
| calcium pantothenate | 2.0 mg/l e.g. 1 mg/l |
| Fe-EDTA, | 10-42.5 mg/l e.g. 21.5 mg/l |
| pyridoxine, | 50 mg/l e.g. 1 mg/l |
| nicotinic acid, | 50 mg/l e.g. 1 mg/l |
| Thiamine | 2.0 mg/l e.g. 1 mg/l |
| Biotin | 2.0 mg/l e.g. 0.1 mg/l |
| BAP | 2.0 mg/l e.g. 0.3 mg/l |
| sucrose | 20-120 g/l e.g. 30 g/l |
| myo-inositol | 10-200 mg/l e.g. 100 mg/l |
| Amino Acid Stock Solution 1000X | 1 ml/L |
| Phytagel (solid media only) | 1.5-3.0 g/l e.g., 2.2 g/l |

Identification of Hormone Balance for Direct Secondary Somatic Embryogenesis

A variety of media were tested to assess the concentrations of plant hormones and stressors to be used in direct secondary somatic embryogenesis, as set forth in the following tables:

TABLE 7

Embryogenic induction media

| CLONE | MEDIA | AMBIENTAL CONDITION | EXPLANT | INOCULUM CONCENTRATION | CONCENTRATION GIBERLINE (MG/L) | CONCENTRATION SUCROSE (g/l) | REPLICATES NUMBER |
|---|---|---|---|---|---|---|---|
| CCN10 | LIQUID CATIE | 21 days in light after 21 days in dark for maturation TEMPERATURE 25° C.-27° C. | COTYLEDOS | 1 PRIMARY EMBRYOS PER 50 ML OF MEDIA | 0 | 40 | 5 |
| | | | | | | 80 | 5 |
| | | | | | 0.2 | 40 | 5 |
| | | | | | | 80 | 5 |
| | | | | | 0.4 | 40 | 5 |
| | | | | | | 80 | 5 |
| | | | | | 0.6 | 40 | 5 |
| | | | | | | 80 | 5 |
| | | | | | 1.0 | 40 | 5 |
| | | | | | | 80 | 5 |

TABLE 8

Development medium (CATIE)

| CLONE | MEDIA | AMBIENTAL CONDITION | EXPLANT | INOCULUM CONCENTRATION | CONCENTRATION BAP (Mg/l) | CONCENTRATION SUCROSE (g/l) | REPLICATES NUMBER |
|---|---|---|---|---|---|---|---|
| CCN10 | LIQUID YASUDA | PHOTOPERIOD 16:8 TEMPERATURE 25° C.-27° C. | COTYLEDOS | 1 PRIMARY EMBRYOS PER 50 ML OF MEDIA | 1.0 | 40 | 5 |
| | | | | | | | 5 |
| | | | | | | | 5 |
| | | | | | | | 5 |
| | | | | | | | 5 |
| | | | | | | 80 | 5 |
| | | | | | | | 5 |
| | | | | | | | 5 |
| | | | | | | | 5 |
| | | | | | | | 5 |

Histological Study—Procedure

Cotyledon explants were collected 40 days after induction and were used for study. Samples were fixed with FAA [10% formalin, 5% acetic acid, 50% ethanol (v/v)] per 8 days. The sample must be previously cut into approximately 0.5 to 1.0 mm. Do three (3) washes of 5 minutes each with distilled water or buffer to remove the fixative. Dewater the material in increasing concentrations of ethanol for at least 1 h of 70%, 85% and 95% at room temperature (incubation time varies with the kind of the material).

Each sample is incubated in 1 ml of 1:1 (v/v) Basic historesin+95% ethanol for 1 h in a desiccator negative pressure on the vacuum pump negative pressure (5-10 psi). The samples are transferred to pre-infiltration solution consisting of 1:1 (resin/activator)+95% ethanol. And incubated in a glass dessicator environmental temperature overnight. The material is transferred to 500 µl solution of basic historesin and must remain for at least 24 hours in refrigerator.

The material is transferred to the inclusion solution. Historesin should be removed from the refrigerator with hardener with an hour of antecedence and placed at environmental temperature. For each form requires nine (9) blocks Historesin, 3.5 ml of basic solution and 0.25 ml activator solution. Distribute in the form until filling it up and leave it in the lab table in environmental temperature for 1 h until the solution is slightly firm to include the material. Then include the vegetal material and leave it in incubator 45° C. per 24 h, after, the material in block is left in environmental temperature per 3 h. The resin blocks are removed from the form and they are pasted in a woody table with 2.5 mm/2.0 mm of area. The samples are cutting in microtome LAICA model MR 1345 with glass knife of 8.0 µm density and stained with 0.5% toluidine blue in 0.1 M phosphate buffer pH 6.5.

Evaluation and Statistical Analysis

Since the experiments were established, evaluations have been performed every 14 days, and some dependent variables like: number of calluses formed, number of normal embryos without callus formation, number of abnormal embryos without callus formation, number of pro-embryogenic masses, number of torpedo embryos, number of heart embryos, number of globular embryos, and overall observations. The Dino-Lite digital microscope premier, AM4113/AD4113 series was used for the observations.

Statistical analysis was performed using the R Core Team (2014) statistical program. R: A language and environment for statistical computing. R Foundation for Statistical Computing, Vienna, Austria.

Results of Analysis of Hormone Balances and Stressor Agents for Direct Secondary Somatic Embryogenesis The experiment was a sequence of mediums where the first was induction medium (Table 7) followed by combination with develop medium (Table 8). The factorial analysis was 5×2, in view of the testing of 2 sucrose concentrations (40 and 80 g/l) and 5 gibberellic acid concentrations (0.0, 0.2, 0.4, 0.6 and 1.0 mg/l), using a completely randomized design.

Figure 2:
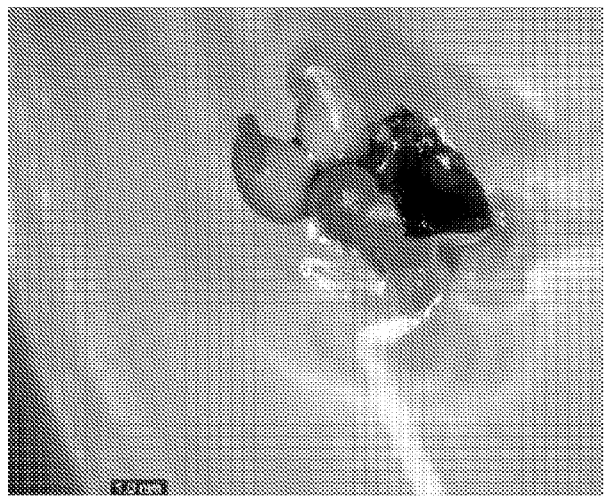
FIG. 2 is a photograph of direct somatic embryos in early torpedo stage, which were treated with 0.6 mg/l gibberellic acid and 40 g/l sucrose.
Figure 3:
FIG. 3 is a photograph of a direct somatic embryo in the mature cotyledonary stage.

The first step for production of direct secondary somatic embryos is believed to be the induction of the competence of cells that was stimulated by stressors in the induction medium. For that, an analysis of the correlation between BAP and sucrose concentrations with the following sequence of mediums containing gibberellic acid for expression and develop embryos in the developing medium. The embryos were expressed and developed in the sequence of mediums. The sequence described below was deemed the best treatment for production of direct secondary embryos:

1) Step 1 induction: 1.0 mg/l BAP with 40 g/l sucrose in light conditions for 40 days for expression somatic embryos (see FIG. 1);

2) Step 2 Expression: 0.6 mg/l Gibberellic acid associated with 40 g/l sucrose in light 21 days for develop and maturation of embryos (see FIG. 2);

3) Step 3 developing and maturation: The same medium as in Step 2, but without gibberellic acid for 3 transferences in darkness. 21-60 days was required for maturation (see FIG. 3).

Figure 4:
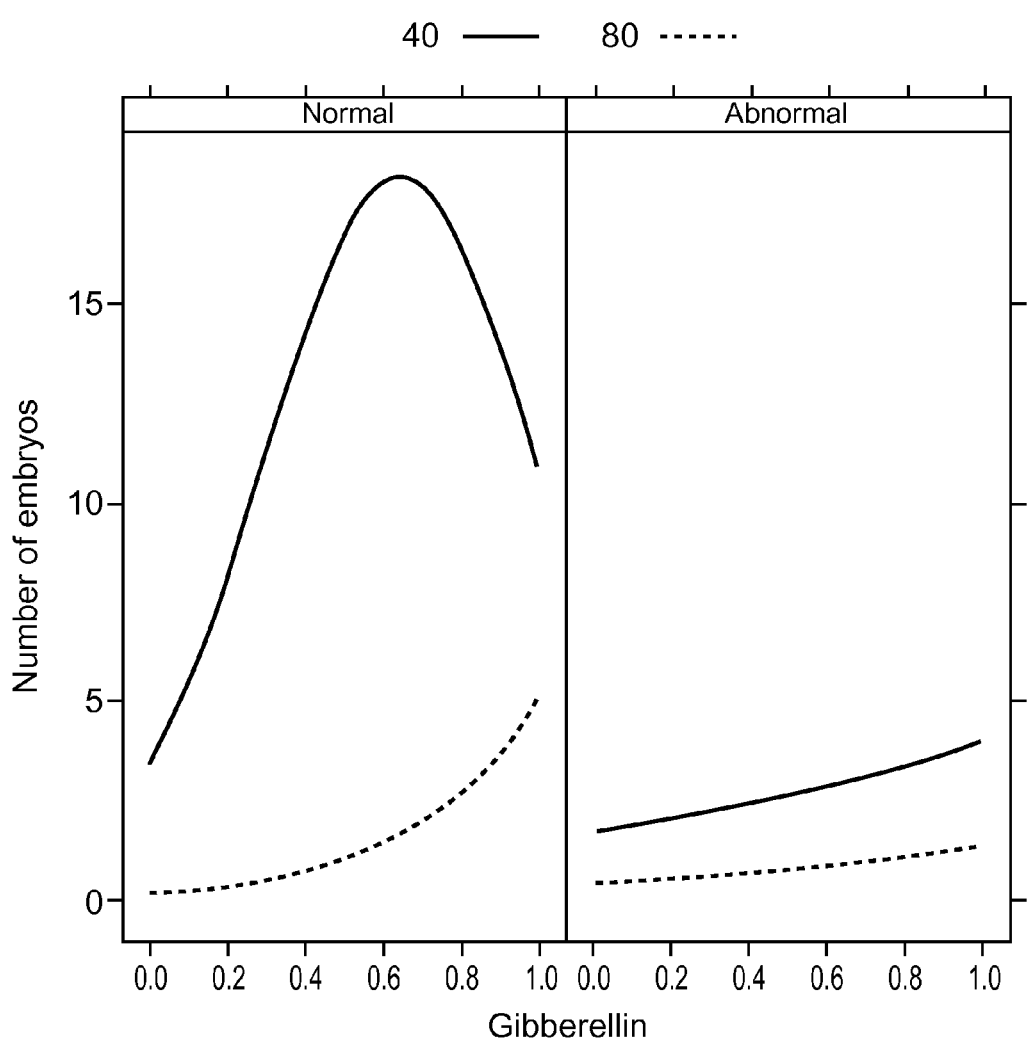
FIG. 4 is a graph of the number of embryos produced in different concentrations of gibberellic acid and sucrose. Gibberellic acid influenced the expression of direct somatic embryos when used in combination with 40 g/L or 80 g/L of sucrose.
Figure 5:
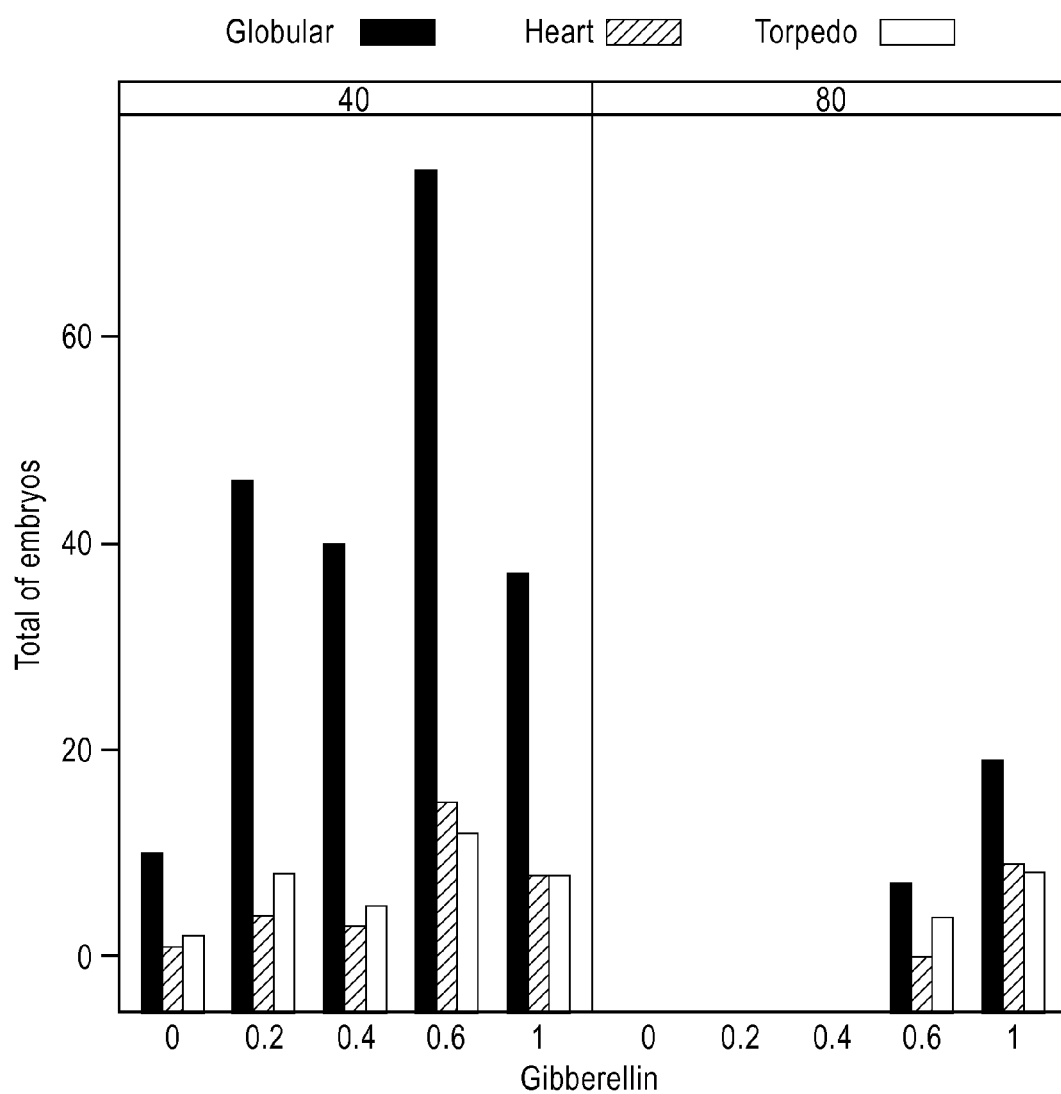
FIG. 5 is a graph of the number of embryos in different stages (globular, heart, and torpedo) in different concentrations of gibberellic acid and sucrose. Histological analysis of cotyledon explants showed that the tissue was composed primarily of parenchymatous and subepidermal cells having high levels of embryogenic activity. The embryonic regions developed large numbers of direct somatic embryos in globular and heart stage after 40 days of culture in induction medium containing 1.0 mg/L BAP with 40 g/L sucrose.
Figure 6A:
FIGS. 6A-6C are photographs that depict the morphological stages of direct somatic embryogenesis.
Figure 6B:
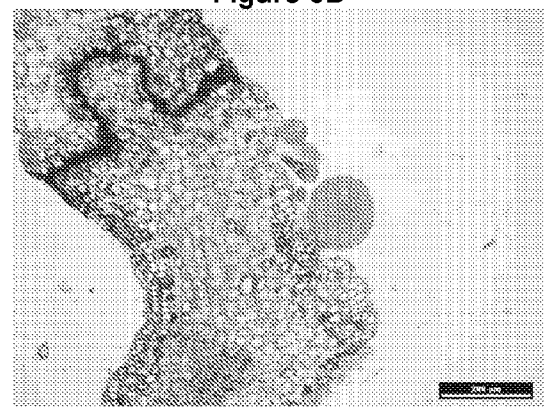
Figure 6C:
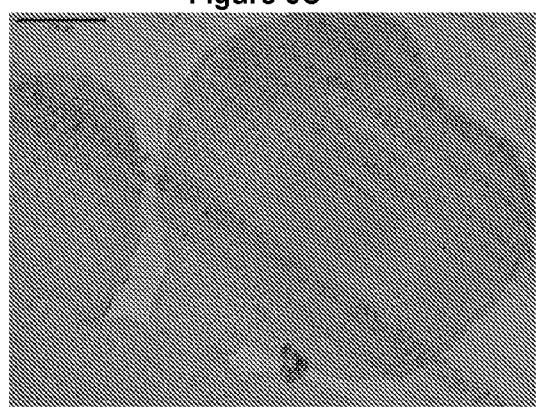

The sequence of mediums mentioned above resulted in 83.3% normal embryos, as compared with the treatment with 1 mg/l of gibberellic acid and 40 g/l of sucrose, which was the treatment that produced the highest quantity of abnormal embryos (see FIG. 4).

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above.

What is claimed:

1. A process for propagating *Theobroma cacao* L., the process comprising:
  (a-1) obtaining primary somatic embryos from *Theobroma cacao* L. explant material, by
    (i) placing the explant material into a first induction medium with exposure to light for a period sufficient to obtain induced primary embryos; and
    (ii) transferring the induced primary embryos into a first development medium and culturing the induced primary embryos with exposure to light for a period sufficient to produce primary somatic embryos by direct somatic embryogenesis;
  (b-1) obtaining secondary somatic embryos from tissue of the primary somatic embryos, by
    (i) placing the tissue of the primary somatic embryos into a second induction medium with exposure to light for a period sufficient to obtain induced secondary embryos,
    wherein the second induction medium in step (b-1)(i) comprises 6-benzylaminopurine (BAP) and sucrose, wherein:
      the BAP in the second induction medium is present in an amount from about 0.5 mg/L to about 1.5 mg/L, and
      the sucrose in the second induction medium is present in an amount from about 20 g/L to about 80 g/L; and
    (ii) transferring the induced secondary embryos into a second development medium and culturing the induced secondary embryos with exposure to light for a period sufficient to produce secondary somatic embryos by direct somatic embryogenesis,
wherein the second development medium comprises gibberellic acid and sucrose, wherein:
the gibberellic acid in the second development medium is present in an amount from about 0.2 mg/L to about 0.8 mg/L; and
the sucrose in the second development medium is present in an amount from about 20 g/L to about 80 g/L; and
(c) transferring the secondary somatic embryos from step (b-1) to a maturation medium to cause maturation of the secondary somatic embryos.

2. The process of claim 1, wherein in step (a-1) the first induction medium comprises a higher concentration of 6-benzylaminopurine (BAP) than the first development medium.

3. The process of claim 1, further comprising, after step (b-1) above and before step (c), transferring the products of step (b-1) to a third development medium suitable for initiation, expression and production of new direct secondary somatic embryos, and incubating therein with exposure to light until the number of secondary somatic embryos therein is increased.

4. The process of claim 1, wherein the explant material for use in step (a-1) comprises petals, staminodes, and epicotyls of primary embryos of *Theobroma cacao* L.

5. The process of claim 1, wherein the medium used in at least one of steps (a-1), (b-1) or (c) is solid.

6. The process of claim 1, wherein the medium used in at least one of steps (a-1), (b-1) or (c) is liquid.

7. The process of claim 1, wherein the temperature during steps (a-1) and/or (b-1) and/or (c) is in the range of from 23-29° C.

8. The process of claim 1, wherein during step (a) and step (b), cultures are in the light for at least 50% of each 24 hour period.

9. The process of claim 8, wherein the photoperiod is a 16 hour:8 hour (light:dark) with a photosynthetic active radiation (PAR) of 50-60 µmol/m² sec.

10. The process of claim 1, further comprising pre-germinating, optionally germinating, and developing embryos obtained by the propagation methods into plantlets.

11. The process of claim 1, further comprising propagating the embryos or plantlets into plants bearing fruit.

12. The process of claim 11, wherein the fruit is removed from the original plant.

13. The process of claim 12, wherein the fruit is processed into a cocoa product.

14. The process of claim 13, wherein the cocoa product is cocoa liquor, chocolate, compound chocolate, chocolate-like substance, cocoa powder or cocoa butter.

15. The process of claim 12, wherein the fruit is partially or fully depulped.

16. The process of claim 15, wherein the partially or fully depulped fruit is fermented using microbiological processes or chemical processes.

17. The process of claim 12, wherein the fruit are dried by exposing the fruit to the sun or an artificial dryer.

18. The process of claim 17, wherein the fruit are further roasted.

19. The process of claim 18, wherein the roasted fruit are winnowed to generate a nib.

20. The process of claim 19, wherein the nib is converted to cocoa liquor or cocoa butter.

21. The process of claim 20, wherein the nib or cocoa liquor is converted to cocoa powder.

22. The process of claim 19, wherein the nib is mixed with sugar.

23. The process of claim 22, wherein the resulting mixture is a paste.

24. The process of claim 23, wherein the paste is refined to generate smaller particle sizes within the paste.

25. The process of claim 20, wherein there is an addition of milk solids.

26. The process of claim 25, wherein the mixture is processed to a milk crumb.

27. The process of claim 22, wherein the mixture is mixed in a conche, optionally with cocoa butter and emulsifier.

28. The process of claim 27, wherein the mixing takes place in a conche.

29. The process of claim 27, wherein the end product is an edible cocoa containing product.

30. The process of claim 1, wherein the BAP is present in an amount of about 1.0 mg/L, the gibberellic acid is present in an amount of about 0.6 mg/L, and the sucrose is present in each of the induction medium and the development medium in an amount of about 40 g/L.

31. The process of claim 17, wherein the artificial dryer is a Samoan dryer, a Buttner dryer, or a platform dryer.

32. The process of claim 27, wherein the conche is a Frissee conch, a Tourell conche, a Macintyre refiner/conche, or a wiener process.

33. The process of claim 28, wherein the edible cocoa containing product is chocolate, compound chocolate, or a chocolate-like substance.

34. The process of claim 20, wherein the liquor or cocoa butter, or a combination thereof, is mixed with sugar.

35. The process of claim 24, wherein the paste is refined using a roller system.

36. The process of claim 1, wherein in step (b-1) the second induction medium comprises a higher concentration of 6-benzylaminopurine (BAP) than the second development medium.

37. The process of claim 1, wherein the *Theobroma cacao* L. is of CCN-10 (CCN10) genotype.

* * * * *